United States Patent [19]

Haines

[11] Patent Number: Plant 6,267

[45] Date of Patent: Aug. 30, 1988

[54] PEACH TREE 'SALEM'

[75] Inventor: Charles W. Haines, Elmer, N.J.

[73] Assignee: Adams County Nursery, Inc., Aspers, Pa.

[21] Appl. No.: 877,772

[22] Filed: Jun. 24, 1986

[51] Int. Cl.[4] ..... A01H 5/00

[52] U.S. Cl. ..... Plt./43

[58] Field of Search ..... Plt./43

*Primary Examiner*—James R. Feyrer

*Attorney, Agent, or Firm*—Frank B. Robb

[57] ABSTRACT

A volunteer seedling found in a block of Loring (unpatented), subsequently found to have vigorous growth, somewhat similar to Loring but superior in that strong, large quantities of budwood are produced which is very resistant to temperatures as low as minus ten degrees F., fruit which ripens five to ten days before Loring and during the fourth picking of RedHaven (unpatented), very productive of fruit, which fruit is blushed red and the tree having demonstrated tolerance to bacterial spot (*Xanthomonas campestris* pruni), in an area where this disease has been known to be severe.

1 Drawing Sheet

This invention relates to a new and distinct variety of peach tree, which was discovered by me as a volunteer seedling being a lone tree in a large tree block of Loring (unpatented) planted on acreage located near Elmer, Upper Pittsgrove Twp., Camden County, N.J.

While the tree is not unlike neighboring Loring trees, in its growth habits, it is nevertheless vigorous as they are, upright and annually manufacturing large quantities of strong budwood. Under severe conditions of winter, when the Loring trees lost most of their buds, the variety of my invention, produced buds which survived −10 degrees F. temperatures providing twelve buds per foot of budwood.

I believe however that the fruit of my new variety, which I have chosen to denominate as "Salem", is the particularly attractive aspect of my new variety, the fruit thereof ripening five to ten days before Loring, and usually during the fourth picking of RedHaven (unpatented). The fruit hereof is extremely large averaging 2.6–3.0 inches, and may be harvested in two or three pickings. The color of the fruit is reddish with a mottled orange-yellow background.

I have caused the tree of my new variety to be asexually reproduced by budding, and found that successive generations of the trees produced thereby, have characteristics which are true and follow those herein described.

In actual production, the tree of my new variety has produced fruit which may be harvested in substantial quantities the yields having increased somewhat over the years, but in many respects being similar to those of Loring trees.

As a matter of fact however, I have found that on the average, over a number of years, the fruit or the quantity of fruit has been noticeably greater than that produced by Loring.

The flowers of my new variety are non-showy, and bloom usually about the time of RedHaven, approximately April 17 to April 25 at the orchard owned by me where the same are grown.

I have found that the tree is substantially demonstrating a tolerance to bacterial spot (*Xanthomonas campestris* pruni), in an area where this disease can be severe.

In the accompanying drawing, the fruit of my new variety is disclosed as viewed from different areas over the surface and one being sectioned to illustrate the color of the flesh.

The leaves disclosed are shown for the shape alone, as to the upper and lower surfaces. The color is not intended to be true since it is not possible to do so where the fruit is disclosed in the same illustration.

The colors in all cases where denominated herein are reproduced in as nearly true conditions as it is possible to make in photographs and color illustrations of this kind.

There follows a detailed description of my new variety, with color terminology and notations in accordance with the Munsell Limit Color Cascade, except where general color terms of ordinary dictionary significance are suitable and adequately describe the same in usually specific detail.

Locality where grown and observed: Elmer Road, Upper Pittsgrove Twp., Salem County, N.J.

Dates of first and last pickings: August 5 to August 20 most recently.

Tree: Large; vigorous; spreading; open; vase formed; hardy; productive and a regular bearer.

*Trunk.*—Stocky; medium size.

*Branches.*—Stocky; medium. Lenticels — moderately numerous and medium size.

*Leaves.*—Length — About 6¼ to 7 inches. Width — About 1¼ to 1⅜ inches. Large size; acuminate; abruptly pointed; medium thickness; smooth. Margin — crenate. Petiole — medium length and medium thickness. Glands — average number three; opposite; medium size; reniform; color — underside of blade 16-10; upperside of blade 16-14; petiole 16-10.

Flower buds: Hardy; medium size.

Flowers: Dates of first and full bloom April 5 to April 10 most recently; medium in earliest; small size.

*Color.*—Pink 37-9.

Fruit: Maturity when described August 5 most recently.

*Size.*—Large; axial diameter approximately 2½ to 3 inches; transverse in suture plane approximately 2⅝ to 3 inches; at right angles to suture plane 2⅝ to 3 inches.

*Form.*—Unform; symmetrical; globose. Suture — shallow; extends from base to beyond but discontinous at apex over entire curcumference. Ventral surface — rounded slightly. Cavity — round, abrupt and circular; slightly elongated in suture place with suture showing on one side. Depth — ½ inch; Breadth — ½ inch. Marking — yellowish green undercolor with mostly red to orange red. Base — retuse. Apex — emarginate. Stem — short; ¼ inch long; medium diameter; pubescent. Skin — medium thickness; flesh — free. Color — Highly blushed red; mostly peach red. Down — moderate.

*Flesh.*—Color — yellowish; mottled with red; surface of pit cavity yellow 30-8 flesh color. Amygadalin — abundant. Juice — abundant. Texture — medium firmness. Fibres — fine. Ripens — evenly. Flavor — mild subacid. Aroma — distant. Eating quality — good.

Stone: Semifree; adheres somewhat to the flesh.

*Size.*—Medium.

*Length.*—1¼ to 1½ inches.

*Thickness.*—⅞ to 1¼ inch.

*Form.*—Acuminate.

*Base.*—Oval.

*Sides.*—Equal.

*Surface.*—Furrowed near base; pitted throughout.

*Color.*—Reddish 31-12.

*Tendency to split.*—Slight in wet season.

Use: Dessert.

Keeping quality: Good.

Resistance to insects and diseases: Good.

Shipping quality: Good.

I claim:

1. A new and distinct variety of peach tree as herein shown and described, characterized as to novelty by the unique combination of vigorous upright growth, ability to manufacture substantial quantities of strong budwood, which enables buds to resist low temperatures, fruit which is very large averaging 2.6 to 3.0 inches harvested in two to three pickings, the color of the flesh of the fruit being yellow, mottled with red, abundant juice being present, ripening evenly, and five to ten days before Loring, the quantity of fruit produced increasing with the age of the tree, and the tree having demonstrated tolerance to bacterial spot (*Xanthomonas campestris* pruni) in an area where such disease can be severe.

* * * * *

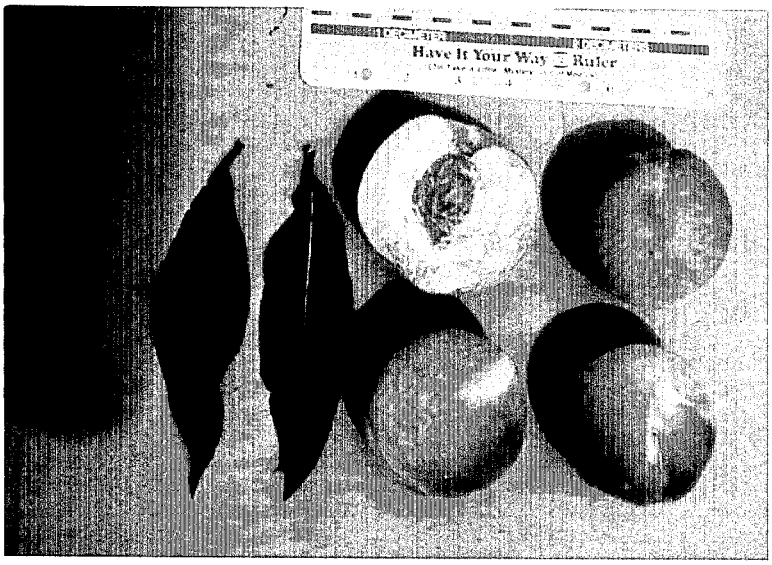
Have It Your Way Ruler